United States Patent [19]

Hnatowich

[11] Patent Number: 4,668,503

[45] Date of Patent: * May 26, 1987

[54] PROCESS FOR LABELING AMINES WITH $^{99m}$TC

[75] Inventor: Donald Hnatowich, Worcester, Mass.

[73] Assignee: Trustees of University of Massachusetts, Amherst, Mass.

[ * ] Notice: The portion of the term of this patent subsequent to Oct. 30, 2001 has been disclaimed.

[21] Appl. No.: 590,833

[22] Filed: Mar. 19, 1984

Related U.S. Application Data

[63] Continuation-in-part of Ser. No. 401,834, Jul. 26, 1982, Pat. No. 4,479,930.

[51] Int. Cl.$^4$ ...................... A61K 43/00; A61K 49/02; A61K 39/00
[52] U.S. Cl. .......................................... 424/1.1; 424/9; 424/85; 436/548; 530/389; 530/391; 530/409; 534/14; 935/107; 935/108
[58] Field of Search ............................... 424/1.1, 9, 85; 436/548; 935/107.8; 534/14; 530/381, 391, 409

[56] References Cited

U.S. PATENT DOCUMENTS 4,479,930 10/1984 Hnatowich .......................... 424/1.1

OTHER PUBLICATIONS

Sundberg et al., J. Med. Chem., 17(1974) 1304–7.

Primary Examiner—Christie M. Nucker
Attorney, Agent, or Firm—Paul J. Cook

[57] ABSTRACT

Amines, including proteins and polypeptides covalently coupled with a chelating agent such as diethylenetriaminepentaacetic acid (DTPA) can be labeled with $^{99m}$Tc in the presence of a stannous reducing agent at near neutral pH by maintaining the protein concentration at a low level and the DTPA concentration at a high level. The $^{99m}$Tc is labeled to the protein through the DTPA sites linked to the protein. Utilizing $^{111}$In labeled proteins as controls, it is shown that the $^{99m}$Tc labeled proteins are labeled at the DTPA sites and that they exhibit in vivo stabilities equal to that of the $^{111}$In labeled proteins.

5 Claims, No Drawings

PROCESS FOR LABELING AMINES WITH $^{99m}$TC

REFERENCE TO RELATED APPLICATION

This application is a continuation-in-part of application Ser. No. 401,834, filed July 26, 1982, now U.S. Pat. No. 4,479,930.

BACKGROUND OF THE INVENTION

Prior to the present invention, proteins such as antibodies have been radiolabeled with iodine. A more attractive approach to the radiolabeling of amines, polypeptide chains and proteins has been the "bifunctional chelate" methods in which a strong chelating group is covalently bonded to the protein which, in turn, is labeled with a variety of chelatable radionuclides. In the resultant product, the protein retains its biological function and the product also retains the radionuclide. When the chelating group chosen forms stable chelates, the radiolabel is likely to be stable in vivo. In addition, its presence will have only a minor effect on the specificity or other functional biochemical characteristics of the protein.

Although methods have been developed for labeling uncoupled proteins with $^{99m}$Tc, both the mechanism of labeling and the site of attachment are unknown. More importantly, the labeled protein is often contaminated with loosely bound or unbound chemical forms of $^{99m}$Tc. To minimize these radiocontaminants, various labeling methods have exposed the protein to acidic conditions, employed long incubation periods and/or required terminal chromatography for purification. In addition to increasing the rate of blood clearance and uptake in several organs, these radiocontaminants may permit exchange of $^{99m}$Tc among plasma proteins.

It has also been proposed to label proteins linked to DTPA with $^{99m}$Tc in the presence of dithionite reducing agent, [Khaw et al, Nuclear Med., vol. 23, 00. 1011-1019 (1982)]. However, it has not been shown that the DTPA groups bound to the protein are labeled with $^{99m}$Tc. Although these methods differ in important respects, they all rely upon the protein to stabilize $^{99m}$Tc in a reduced oxidation state and prevent both re-oxidation and the formation of radiocolloids. Proteins may be only partially successful in this judging by in vivo instabilities reported in the prior art: when the biological behavior of $^{99m}$Tc-labeled proteins have been compared to radioiodinated proteins, with very few exceptions, $^{99m}$Tc was found to clear more rapidly from blood. Other investigations have reported increased liver accumulation.

Since DTPA-coupled proteins may be stably labeled with $^{111}$In, the use of DTPA-coupled proteins for $^{99m}$Tc labeling could offer the advantage of greater in vivo stability than that presently attainable. However, investigations into the labeling of coupled proteins with $^{99m}$Tc, it has been observed that proteins can compete with DTPA for $^{99m}$Tc [Lanteigne et al, J. Nuc. Med., 24:23 (1983) Abstract].

Overall, therefore, there is a long demonstrated need for a simple and efficient means for utilizing a bifunctional chelating agent for binding radiolabels to amines, polypeptides and proteins and other medically important compounds such that their radiolabeled forms are stable in vivo and retain their specific biological activities to a substantial degree.

SUMMARY OF THE INVENTION

This invention is based upon the discovery that DTPA coupled proteins can be labeled at the DTPA sites with technetium-99m despite the competition for technetium-99m by the protein. The labeling is effected at near neutral pH with stannous reducing agent and by controlling the relative concentrations of the protein and DTPA during coupling with the technetium-99m. This invention provides substantial advantages over prior art processes since labeling is effected with the DTPA rather than the protein and the process is performed at neutral pH so that the protein is not denatured and the technetium-99m is not decoupled easily.

In accordnace with this invention, radiolabeled compositions are prepared by reacting, in a first step, an amine with a chelating agent capable of being coupled to an amine and capable of chelating technetium-99m. Representative chelating agents include ethylenediamine tetraacetic acid (EDTA), diethylenetriamine tetraacetic acid (DTPA) or their dianhydrides of the formula

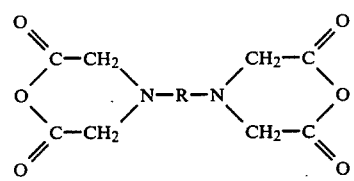

wherein R is a linking group containing from 1 to 25 carbon atoms and which can include nitrogen atoms and/or carboxyl groups or other groups which do not denature proteins or peptides and which do not interfere with the hydrolyzed dicyclic dianhydride ability to chelate technetium-99m. The concentration of amine to DTPA is maintained at a low level so that subsequent non-specific labeling of technetium-99m to the amide is minimized while direct labeling of technetium-99m to DTPA bound to the amine is maximized. In the second step, the amide and DTPA are reacted with technetium-99m reduced with stannous ion at a pH between about 6 and 7.

DETAILED DESCRIPTION OF THE EMBODIMENTS

In its broadest aspect, the invention is a novel method of radiolabeling amines with technetium-99m. The composition provided by this invention comprises three parts: Technetium-99m, a chelating agent capable of covalently binding to a primary or secondary amine and of chelating technetium-99m and a primary or secondary amine. In order to obtain a full and clear comprehension of the many possible embodiments within the scope of the present invention, the chelating agent and amine will be described individually.

Chelating Agents

Those compositions suitable as chelating agents include DTPA, EDTA or their dianhydrides which, prior to being hydrolyzed, are represented generally by the structure

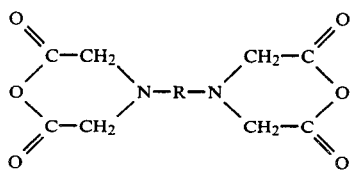

wherein R is defined above and is preferably CH₂CH₂N(CH₂(COH)CH₂CH₂ or ethylene. The preferred chelating agents are hydrolyzed forms of the cyclic dianhydrides of ethylenediaminetetraacetic acid (hereinafter EDTA) and diethylenetriaminepentaacetic acid (hereinafter DTPA).

Chelating agents having the general structural formula represented above are, in their cyclic anhydride forms, efficient coupling agents able to couple to many different amines, such as polypeptides or proteins. Coupling efficiency is defined herein as that number of dicyclic dianhydride molecules which form amide bonds with the amine divided by the total number of cyclic dianhydride molecules added initially. It is apparent that R in the general formula will include many simple and complex combinations of carbon, hydrogen, nitrogen and other atoms. Accordingly, all chelating agents set forth above and having a coupling efficiency greater than 1% are deemed to be useful within the scope of this invention.

Amines, Polypeptides and Proteins

An almost infinite variety of primary or secondary amines in non-aqueous and aqueous media will be coupled by the dicyclic dianhydride chelating agents desceibed herein. Examples of suitable primary or secondary amines are those polypeptide chains and proteins having immunological functions such as antibodies and fragments of antibodies such as F(ab) and F(a')₂ fragments, all of which form stable amides with the dicyclic dianhydride which amides are capable of chelating a metal radionuclide. Other compounds of interest such as plasma proteins, typically albumins and fibrinogen, also form stable amides.

In view of the broad and varied class of compounds which may be bound by these chelating agents and then chelated to a radionuclide to form a stable radiolabeled product in vivo, all chemical compositions having at least one amine group available for binding as an amide bond with these anhydrides are deemed to be within the scope of the present invention.

For purposes of illustrative clarity and ease of comprehension, only one of the preferred chelating agents—the dicyclic dianhydride of DTPA—will be referred to hereinafter. It shall be understood, however, that the use of this particular chelating agent for descriptive purposes shall not restrict nor limit the use or applicability of other chelating agents described above. It is to be recognized, however, that the other chelating agents set forth above may be less efficient as chelating agents than DTPA.

Radioisotope labeling with technetium-99m is effected at neutral pH between about 6 and 7 in order to prevent denaturation of the amine. The technetium-99m is added to the amine in reduced form with stannous ion, preferably as stannous chloride. In accordance with this invention, it has been found necessary to regulate the relative concentrations of the amine and the chelating agent, e.g. DTPA since it has been determined that technetium-99m becomes bound to the amine, particularly a protein, even in the presence of DTPA. It is preferred that the technetium-99m bind to the DTPA since the bond thereto is likely to be much stronger than the bond between technetium-99m and the protein and therefore, the probability of decoupling of the technetium-99m when administered to a patient is far less. The extent with which this competition for the technetium-99m will vary with the particular amine and particular chelating agent and can be determined empirically such as by the method shown in the example herein. In accordance with this invention, it is necessary that the relative molar concentrations of chelating agent coupled to protein and free protein be adjusted such that the protein is preferentially labeled with technetium-99m at the DTPA sites. The specific relative concentration utilized in a particular system will vary depending upon the particular protein or amine being radiolabeled. The concentration of chelating agent, e.g., DTPA, should not be so high as to denature the protein, but should not be so low that the radiolabel binds directly to the protein. Suitable relative concentrations of protein to chelating agent can be readily determined by determining whether the protein is not denatured and by determining the degree of radiolabel decoupling, if any. In addition, it is necessary that the mole ratio of chelating agent to the stannous reducing agent be less than 1 in order to prevent non-specific binding of tin directly to the protein.

As evidenced by the studies described hereinafter, the present invention provides unique and valuable advantages not previously available with prior art methodologies employing technetium-99m as a label. The coupled amine may be purified from the hydrolysis products before addition of any radioactivity, thereby avoiding the need to handle radioactive samples during the purification process. The coupling with the chelating agent is efficient and simple after which the coupled product maintains its ability to bind a technetium-99m label subsequently for a long period of time of at least a month. Such coupled and purified protein solutions may be stored in buffer at 4° C. without detectable or deleterious effects for at least four months and then radiolabeled only when required, and will not require purification after labeling with $^{99m}$Tc.

The following example illustrates the present invention and is not intended to limit the same.

EXAMPLE I

Measurement of Relative Formation Constants

Investigations into the competition of proteins and DTPA for $^{99m}$Tc require that the activity in each chemical form be determined. Because instant thin layer chromatography (ITLC) will easily separate free DTPA from protein, competition studies in this work have been performed with free DTPA in the presence of uncoupled proteins rather than with DTPA-coupled proteins. To validate the model, it is necessary to show that the constants for the formation of the $^{99m}$Tc chelates of a monoamide of DTPA (representing coupled DTPA) and free DTPA are similar.

The hexadecylamine monoamide of DTPA was synthesized to show that the constants for the formation of the $^{111}$In chelates of the monoamide and DTPA are essentially identical. The same procedure was employed in this work with $^{99m}$Tc.

Solutions containing different concentrations of the monoamide and DTPA in the range 0–0.1 mg/ml were prepared in 0.1 M acetate buffer at pH 6 and were purged with nitrogen. Approximately 25 μg of stannous chloride (SnCl$_2$.2H$_2$O) was then added from a 3 mg/ml solution at pH 1. Fifteen minutes later, 100–200 μCi of $^{99m}$Tc-pertechnetate was added and, 15 minutes later, the samples were spotted for analysis by ascending paper chromatography (Whatman No. 1 paper, 0.1 M acetate buffer, pH 6). Labeled monoamide remains near the origin while labeled DTPA migrates to the solvent front. Each paper was cut in half and counted separately in a NaI(Tl) well counter. Analysis on ITLC with acetone eluant showed that contamination with pertechnetate was less than 5% in all samples. Re-analysis of several samples at 24 hours showed that equilibrium had been attained in the first analysis.

When the results are plotted as monoamide/DTPA radioactivity ratio (ordinate) vs. the monoamide/DTPA radioactivity ratio (abscissa), a linear regression analysis yields a slope of 0.20 (correlation coefficient 0.97, N=8). Under the conditions of labeling, therefore, the $^{99m}$Tc formation constant for the monoamide of DTPA is roughly 5 times larger than that of DTPA.

Further confirmation that the formation constants are similar was obtained by HPLC analysis of coupled but unpurified IgG preparations labeled with both $^{111}$In and $^{99m}$Tc. The concentration of DTPA was sufficient to render insignificant any competition by the protein for reduced $^{99m}$Tc. Under the conditions of the measurement, the $^{99m}$Tc activity on the protein was 1.7 (range 1.3–2.0) times higher than that of $^{111}$In. Since $^{111}$In distributes among coupled and free DTPA according to their concentrations, these results that show the the constant for the formation of $^{99m}$Tc- coupled DTPA is only slightly higher than that of free DTPA.

Labeling DTPA at Low Concentrations

When coupled at one DTPA group per protein molecule, a solution containing 20 mg/ml of IgG antibody will contain approximately 50 μg/ml of DTPA, whereas solutions at lower concentrations or of proteins with higher molecular weight will contain less DTPA. Consequently, methods of labeling DTPA with $^{99m}$Tc at these concentrations were investigated. Since an important object of this investigation was the radiolabeling of protein under mild conditions, the use of solutions more acidic than pH 6 was not considered.

Solutions containing 25, 50 and 100 μg of free DTPA in one milliliter of 0.1 M acetate buffer at pH 6.0 were prepared and purged. To each was added 5.3 μg of stannous ion (DTPA/tin molar ratio 1.5 or greater), and, after 10 minutes, 0.5–1.0 mCi of $^{99m}$Tc-pertechnetate was added. All samples were analyzed 15 minutes later by ascending paper chromatography (Whatman No. 1 paper, 0.1 M acetate buffer eluant, pH 6) for labeled DTPA (Rf 0.95), pertechnetate (Rf 0.7) and colloids (Rf 0.0). The identical study was also performed in 0.1 M Hepes buffer at pH 7.0. In addition, samples containing 100 μg/ml of DTPA were labeled with $^{99m}$Tc at pH 6.5 with 0.4 M dithionite and at pH 8.0 with 0.4 M sodium borohydride in which the DTPA was present during reduction.

The highest percentages of activity present as labeled DTPA was obtained at pH 6 where the 25, 50 and 100 μg/ml solutions were labeled 81±1%, 89±1% and 91±1%, respectively. At pH 7 with stannous reduction, these values were 40±7%, 59±7% and 80±1%. Only 17±7% of the activity was present as labeled DTPA in the case of borohydride reduction while with dithionite this value was 58±2%. In all cases, the remaining activity was present entirely as radiocolloids.

DTPA Competition Studies

The eight proteins, set forth below, were investigated including serum albumin in which the sulfhydryl groups were blocked with Ellman's reagent. Solutions were prepared containing 20 mg/ml of each protein and 100 μg/ml of free DTPA in nitrogen-purged 0.1 M acetate buffer at pH 6. An aliquot of each solution was labeled with 50 μCi of $^{111}$In by adding the activity as the acetate complex. The remaining solutions were labeled with $^{99m}$Tc by adding stannous ion to a concentration of 15 μg/ml (DTPA/tin molar ratio about 2) followed 10 minutes later by 1–2 mCi of $^{99m}$Tc-pertechnetate. The samples were analyzed 10 minutes later by thin layer chromatography (ITLC) with 0.1 M acetate eluant for labeled protein and colloid (Rf 0) and DTPA (Rf 0.9). Analysis of each sample for $^{99m}$Tc-pertechnetate by ITLC (acetone eluant) showed that typically only 5% of the activity was in this chemical form while in one sample this value was 8%. The results of this study are presented in Table I.

In Vivo Studies

Both lysosyme and IgG were coupled with DTPA using the cyclic anhydride by the method of Hnatowich et al, *Int. J. Appl. Rad. Isotopes,* vol. 33, pp. 327–332, 1982. Analysis by high performance liquid chromatography (HPLC) of an aliquot of each sample after labeling with a tracer quantity of $^{111}$In showed that the lysosyme was coupled with an average of 0.6 DTPA per molecule while for IgG this value was 5.4. The lysosyme preparation was purified from free DTPA on a 15×1 cm Sephadex G 25 column while the IgG preparation was purified on a Roche-CEA G 50 column. The eluant in both cases was 0.1 M acetate at pH 6. The protein concentration in each purified sample was determined by UV absorption measurements at 280 nm. The lysosyme preparation contained 9.6 mg/ml of protein and, therefore, 106 μg/ml of coupled DTPA, while the IgG preparation contained 6.4 mg/ml of protein and 77 μg/ml of coupled DTPA.

About one third of each preparation was labeled with $^{111}$In acetate and the remainder was labeled with $^{99m}$Tc. In the case of lysosyme, 10 μg of stannous ion (DTPA/tin molar ratio about 3.2) was added to 1 ml of the degassed solution, and, 10 minutes later, 2.8 mCi of $^{99m}$Tc-pertechnetate was added. In the case of IgG, 6 μg of stannous ion (DTPA/tin molar ratio about 3.9) was added to 1 ml of the degassed solution, and, 10 minutes later, 3.3 mCi of $^{99m}$Tc-pertechnetate was added. The $^{99m}$Tc-labeled protein samples were found to contain less than 5% $^{99m}$Tc-pertechnetate. The analysis of both the $^{111}$In and $^{99m}$Tc-labeled proteins by HPLC showed all samples to be 92–95% radiochemically pure. All four samples were diluted to a concentration of 1.5 mg/ml with 0.05 M bicarbonate buffer, 0.9% NaCl, pH 7.5 and 0.1 ml was injected via the tail vein into each of five male CD-1 mice. The animals receiving lysosyme were sacrificed at one hour post injection while those receiving IgG were sacrificed at two hours. These early time periods were selected to avoid any complications which would arise from redistribution of the labels after catabolism of the proteins. The tissue samples were removed for weighing and were counted against a standard of the injectate. The results are presented in percent injected dose per gram of tissue and blood in Table II for lysosyme and Table III for IgG.

In the case of IgG, as a further control, the identical labeling study was performed on uncoupled protein. A 1.0 ml solution containing 6.6 mg of the protein in purged acetate buffer was prepared. To this solution 5.4 μg of stannous ion was added and, 15 minutes later, 4.5 mCi of $^{99m}$Tc-pertechnetate was added. Analysis showed that less than 2% of $^{99m}$Tc-pertechnetate was present. The sample was diluted to a protein concentration of 1.5 mg/ml in the bicarbonate buffer and HPLC analysis showed the preparation to be greater than 95% radiochemically pure at injection. The results of this study are also presented in Table III.

Labeling proteins in which strong chelating groups have been attached has the potential of eliminating these difficulties. As shown in the example, free DTPA may be labeled at low concentration by stannous reduction and this may be accomplished rapidly at pH values near neutrality (in the absence of the strong chelating groups, these conditions would result in the formation of tin colloids labeled with $^{99m}$Tc).

Under the conditions used herein, it was possible to label DTPA in the presence of most of the proteins investigated. Furthermore, lowering the protein concentration and raising the concentration of DTPA would have only improved matters such that most, if not all of the proteins, could be labeled. Lysosyme and IgG were investigated more thoroughly; the former because it shows little competition with DTPA and the latter because of its importance. In both cases, the protein concentration was reduced below that used in the competition studies, and, in the case of IgG, more than 5 groups were attached to each molecule to increase the DTPA concentration. In each case, the concentration of stannous ion was much less than that normally used to label uncoupled proteins and was less than that required to saturate the DTPA groups.

The results obtained for lysosyme (Table II) show that at one hour post injection, the biodistribution of $^{111}$In and $^{99m}$Tc are identical. We believe that this result shows conclusively that both labels are chelated to the DTPA groups. The results obtained for IgG (Table III) at 2 hours post injection also show agreement for the two labels in most tissues. The only significant differences are in kidneys and blood in which the $^{99m}$Tc levels are elevated. We believe that these results also demonstrate that in the case of this protein as well, the labels are attached to the DTPA groups but, because of the greater competition of IgG over lysosyme for $^{99m}$Tc, some activity in the former protein preparation may be bound nonspecifically. Additional evidence that the label is attached to the DTPA groups is evident from comparing the biodistribution results for $^{99m}$Tc labeled to coupled and uncoupled IgG (Table III). Significant differences in accumulation are apparent in blood and each tissue type other than stomach.

TABLE I

PERCENTAGE $^{111}$In AND $^{99m}$Tc CHELATED TO FREE DTPA IN THE PRESENCE OF VARIOUS PROTEINS. MEAN VALUE WITH RANGE IN PARENTHESIS.

| Protein | $^{111}$In-DTPA (%) | $^{99m}$Tc-DTPA (%) |
|---|---|---|
| Pepsin | 96 (94–98) | 88 (87–88) |
| Chymotrypsin | 97 (96–98) | 81 (81–81) |
| Lysosyme | 98 (96–99) | 73 (71–75) |
| HSA | 97 (97–97) | 44 (44–45) |
| HSA (SH blocked) | 96 (94–98) | 41 (37–44) |
| IgG | 99 (98–100) | 36 (35–38) |
| Myoglobin | 99 (98–99) | 7 (7–9) |
| Transferrin | 97 (97–97) | 7 (6–8) |

TABLE II

BIODISTRIBUTION IN NORMAL MICE AT 1 HOUR POST INJECTION FOR BOTH $^{111}$In AND $^{99m}$Tc LABELED DTPA-COUPLED LYSOSYME. PERCENT INJECTED DOSE PER GRAM WITH ONE S.D. (N = 5)

| Organ | $^{111}$In-DTPA-Lysosyme | $^{99m}$Tc-DTPA-Lysosyme |
|---|---|---|
| Heart | 0.39 ± 0.03 | 0.40 ± 0.06 |
| Lung | 0.71 ± 0.13 | 0.87 ± 0.14 |
| Liver | 2.40 ± 0.29 | 2.30 ± 0.22 |
| Spleen | 0.41 ± 0.05 | 0.43 ± 0.01 |
| Kidney | 163.0 ± 14.0 | 157.0 ± 16.0 |
| Stomach | 0.44 ± 0.21 | 0.30 ± 0.10 |
| Blood | 0.51 ± 0.10 | 0.65 ± 0.17 |

TABLE III

BIODISTRIBUTIONS IN NORMAL MICE AT 2 HOURS POST INJECTION FOR $^{111}$In AND $^{99m}$Tc LABELED DTPA-COUPLED IgG AND FOR UNCOUPLED IgG LABELED WITH $^{99m}$Tc. PERCENT INJECTED DOSE PER GRAM WITH ONE S.D. (N = 5)

| Organ | $^{111}$In-DTPA-IgG | $^{99m}$Tc-DTPA-IgG | $^{99m}$Tc-IgG |
|---|---|---|---|
| Heart | 3.42 ± 0.56 | 4.16 ± 0.59 | 1.40 ± 0.23 |
| Lung | 3.13 ± 0.39 | 3.79 ± 0.95 | 1.74 ± 0.30 |
| Liver | 8.32 ± 0.93 | 9.86 ± 1.46 | 5.63 ± 0.92 |
| Spleen | 2.15 ± 0.25 | 2.71 ± 0.41 | 1.74 ± 0.21 |
| Kidney | 3.07 ± 0.45 | 6.28 ± 1.41 | 13.2 ± 2.0 |
| Stomach | 1.06 ± 0.20 | 1.35 ± 0.25 | 1.22 ± 0.49 |
| Blood | 14.9 ± 0.7 | 19.2 ± 1.6 | 5.34 ± 0.48 |

I claim:

1. A process for making a technetium-99m labeled composition comprising the steps of:

preparing a chelating agent having the formula

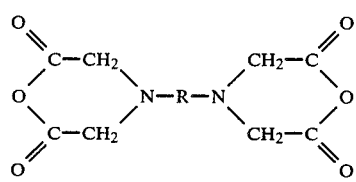

wherein R is a linking moiety comprising between 1 and 25 carbon atoms;

mixing said chelating agent with a host composition selected from the group consisting of an amine, a protein and a polypeptide to covalently link the chelating agent to the host composition, at a ratio of chelating agent to post composition to effect Preferential binding of the technetium-99m to the chelating agent coupled to the host composition while preventing denaturation of the host composition;

mixing the said host composition covalently linked with said chelating agent with stannous tin at a mole ratio of chelating agent to stannous tin of less than about 1 and at a pH between 6 and 7; and mixing technetium-99m with said covalently linked post composition and stannous tin.

2. The method as recited in claim 1 wherein said chelating agent is selected from the group consisting of the dicyclic dianhydride of diethylenetriaminepentaacetic acid, the dicyclic dianhydride of ethylenediaminetetraacetic acid, diethylenetriaminepentaacetic acid and ethylenediaminetetraacetic acid.

3. The method as recited in claim 1 wherein said host composition is selected from the group consisting of a polypeptide and a protein.

4. The method of either one of claims 1 or 2 wherein the host composition is an antibody.

5. The method of either one of claims 1 or 2 wherein the host composition is a plasma protein.

* * * * *